(12) United States Patent
Wagner et al.

(10) Patent No.: US 6,548,043 B1
(45) Date of Patent: *Apr. 15, 2003

(54) MEASUREMENT OF GASTRIC EMPTYING

(75) Inventors: David A. Wagner, Nashua, NH (US); Keith J. Goodman, Nashua, NH (US); Daniel L. Bolt, Medford, MA (US)

(73) Assignee: Metabolic Solutions, Inc., Nashua, NH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/366,358

(22) Filed: Aug. 3, 1999

(51) Int. Cl.[7] .......................... A61K 51/00; A61K 47/00
(52) U.S. Cl. .................... 424/1.81; 424/1.11; 424/1.73; 424/439; 424/1.65; 424/9.1; 424/1.81; 600/532; 600/534
(58) Field of Search ................ 424/1.11, 1.81, 424/439, 1.73, 1.65, 9.1; 600/532, 534

(56) References Cited

U.S. PATENT DOCUMENTS

| | | | |
|---|---|---|---|
| 3,867,099 A | 2/1975 | Forrester | 23/259 |
| D304,232 S | 10/1989 | Fuller | D24/17 |
| 4,947,861 A | 8/1990 | Hamilton | 128/719 |
| 4,985,232 A | 1/1991 | Jacobssen | 424/4.1 |
| 5,026,027 A | 6/1991 | Hamilton | 251/301 |
| 5,071,769 A | 12/1991 | Kundu et al. | 436/128 |
| 5,081,871 A | 1/1992 | Glaser | 73/863.23 |
| 5,140,993 A | 8/1992 | Opekun, Jr. et al. | 128/730 |
| 5,211,181 A | 5/1993 | Delente | 128/730 |
| 5,291,898 A | 3/1994 | Wolf | 128/719 |
| 5,327,901 A | 7/1994 | Delente | 128/730 |
| 5,361,772 A | 11/1994 | Murnick et al. | 128/730 |
| 5,432,094 A | 7/1995 | Delente | 436/127 |
| 5,465,728 A | 11/1995 | Phillips | 128/730 |
| 5,467,776 A | 11/1995 | Hamilton | 128/730 |
| 5,707,602 A | 1/1998 | Klein | 424/1.17 |
| 5,785,949 A | 7/1998 | Klein | 424/1.81 |
| 5,848,975 A | 12/1998 | Phillips | 600/532 |
| 6,013,294 A * | 1/2000 | Bunke et al. | 426/120 |
| 6,432,382 B1 * | 8/2002 | Mehta | 424/9.1 |

FOREIGN PATENT DOCUMENTS

| | | |
|---|---|---|
| WO | WO0061197 | 10/2000 |

OTHER PUBLICATIONS

Maes et al Gut 1995; 36: 183–188, 1995.*

B.D. Maes et al., Pharmacological modulation of gastric emptying rate of solids as measured by the carbon labeled octanoic acid breath test: influence of erythromycin and propantheline, *Gut*, vol. 35, p. 333–337, 1994.

B.D. Maes et al., Gastric Emptying Rate of Solids in Patients with Nonulcer Dyspepsia, *Digestive Diseases and Sciences*, vol. 42, No. 6, p. 1158–1162, Jun. 1997.

L. Duan et al., Influence of Cisapride on Gastric Emptying of Solids and Liquids Monitored by $^{13}$C Breath Tests; *Digestive Diseases and Sciences*, vol. 40, No. 10, p. 2200–2206, Oct. 1995.

D. Ziegler et al., [$^{13}$C]Octanoic acid breath test for non–invasive assessment of gastric emptying in diabetic patients: validation and relationship to gastric symptoms and cardiovascular autonomic function, *Diabetologia*, vol. 39, p. 823–830, 1990.

(List continued on next page.)

Primary Examiner—Russell Travers
Assistant Examiner—S Sharareh
(74) Attorney, Agent, or Firm—Jenken & Gilchrist

(57) ABSTRACT

A meat-free, algae-free, standardized, test meal kit used in the measurement of delayed gastric emptying is provided. The kit contains at least a standardized test meal dry mix and tracer. A method of using the kit is also provided.

17 Claims, 4 Drawing Sheets

OTHER PUBLICATIONS

J.R. Malagelada, Functional Dyspepsia, Insights on Mechanisms and Management Strategies, *Gastroenterology Clinics of North America*, vol. 25, No. 1, p. 103–112, Mar. 1996.

Y.F. Ghoos et al., Measurement of Gastric Emptying Rate of Solids by Means of a Carbon–Labeled Octanoic Acid Breath Test, *Gastroenterology*, vol. 104, p. 1640–1647, 1993.

M.B. Fennerty et al., The Diagnosis and Treatment of Gastroesophageal Reflux Disease in a Managed Care Environment, *Arch Intern Med.*, vol. 156, p. 477–484, Mar. 11, 1996.

M. Scaillon et al., Transit Tests, Publication unknown, Chp. 16.

S. Vigneri et al., A Comparison of Five Maintenance Therapies for Reflux Esophagitis, *The New England Journal of Medicine*, vol. 333, No. 17, p. 1106–1110, Oct. 26, 1995.

L.M.A. Akkermans et al., Gastric Motility and Emptying Studies with Radionuclides in Research and Clinical Settings, *Digestive Diseases and Sciences*, vol. 39, No. 12, p. 95S–96S, Dec. 1994 Supplement.

H.P. Parkman et al., Gastroparesis: diagnostic and Therapeutic Management, *Practical Gastroenterology*, vol. 17, No. 2, p. 18–22, 24–27, Feb. 1993.

M. Horowitz et al., Gastroparesis: Diagnosis and Management, *Scand J. Gastroenterol*, vol. 30, Supp. 213, p. 7–16, 1995.

D.G. Colin–Jones, Dyspepsia Update, *Scand J. Gastroenterol*, vol. 30, Supp. 210, p. 32–35, 1995.

A.M. Caballero–Plasencia et al., Gastroparesis of Digestible and Indigestible Solids in Patients with Insulin–Dependent Diabetes Mellitus or Functional Dyspepsia, *Digestive Diseases and Sciences*, vol. 39, No. 7, p. 1409–1415, Jul. 1994.

H. Abrahamsson, Gastrointestinal motility disorder in patients with diabetes mellitus, *Journal of Internal Medicine*, vol. 237, p. 403–409, 1995.

H.P. Parkman et al., Role of Nuclear Medicine in Evaluating Patients With Suspected Gastrointestinal Motility Disorders, *Seminars in Nuclear Medicine*, vol. 25, No. 4, p. 289–305, 1995.

J.C. Urbain et al., Recent Advances in Gastric Empying Scintigraphy, *Seminars in Nuclear Medicine*, vol. 25, No. 4, p. 318–325, 1995.

R.W. McCallum et al., Gastric Emptying in Patients with Gastroesophageal Reflux, Publication Unknown, p. 285–291, 1981.

A. Keshavarzian et al., Gastric Emptying in Patients with Severe Reflux Esophagitis, *The American Journal of Gastroenterology*, vol. 86, No. 6, p. 738–742, 1991.

J.P. Galmiche et al., The Pathophysiology of Gastro–oesophageal Reflux Disease: An Overview, *Scan J. Gastroenterol*, vol. 30, Supp. 211, p. 7–18, 1995.

B.D. Maes et al., Combined carbon–13–glycine/carbon–14–octanoic acid breath test to monitor gastric emptying rates of liquids and solids, *J. Nucl. Med.*, vol. 35, No. 5, p. 824–31, 1994, abstract only.

B.D. Maes et al., Influence of octreotide on the gastric emptying of solids and liquids in normal healthy subjects, *Aliment Pharmacol. Ther.*, vol. 9, No. 1, p. 11–18, 1995, abstract only.

E. Schvarcz et al., Hypoglycemia increases the gastric emptying rate in healthy subjects, *Diabetes Care*, vol. 18, No. 5 p. 674–676, 1995, abstract only.

M.A. Evans, Gastric emptying rate in the elderly: implications for drug therapy, *J. Am. Geriatr.*, vol. 29, No. 5 p. 201–205, 1981, abstract only.

S. Holt et al., Alcohol absorption, gastric emptying and a breathalyser, *Br. J. Clin. Pharmacol.*, vol. 9, No. 2, p. 205–208, 1980, abstract only.

H. Naveri et al., Gastric emptying and serum insulin levels after intake of glucose–polymer solutions, *Eur. J. Appl. Physiol.*, vol. 58, No. 6, p. 661–665, 1989, abstract only.

O.U. Petring et al., Inter– and intrasubject variability of gastric emptying in healthy volunteers measured by scintigraphy and paracetamol absorption, *Br. J. Clin. Pharmacol.*, vol. 29, No. 6, p. 703–708, 1990, abstract only.

S. Mossi et al., Gastric emptying of liquid meals measured noninvasively in humans with [13C] acetate breath test, *Dig. Dis. Sci,*, vol. 39, Supp. 12, p. 107S–109S, 1994, abstract only.

W. M. Davis, Impact of gender on drug responses, Drug Topics Oct. 5, 1998, Information Access Company, a Thomson Corporation Company, 1998.

* cited by examiner

MEASUREMENT OF GASTRIC EMPTYING

BACKGROUND OF THE INVENTION

1. Field of the Invention

This invention relates to a standard test meal kit that is used in the diagnosis of gastrointestinal disorders characterized by changes in the rate of gastric emptying. The kit contains at least a test meal in the form of a dry mix and a tracer. The test meal dry mix is both meat-free and algae-free, and thus is more palatable than the prior art test meals. The tracer may be combined with the test meal dry mix, or preferable, is provided separate. The kit components may also include a container for mixing and cooking the test meal, a breath collection device, including multiple evacuated tubes, juice or water for reconstituting the test meal, a stirring implement, a temperature indicator, sample labels and a cooking device such as a portable convection oven or microwave.

The test meal is standardized in several respects, including caloric content, volume, carbohydrate, fat and protein proportions, method of preparation and method of administration. The test meal is packed in a stable dry mix form, which can be easily shipped and stored indefinitely at room temperature. The test meal is used with a non-radioactive tracer molecule, such as $^{13}$C-sodium octanoate, which may be provided separate from the dry mix, thus minimizing concerns about stability and FDA regulation. The test meal is reconstituted on site with liquid and tracer, cooked, cooled, administered to a patient, and followed by an appropriate diagnostic measurement, such as the $^{13}CO_2$ breath test.

2. Background of the Invention

Delayed gastric emptying affects tens of millions of patients who are diagnosed with various functional gastrointestinal disorders, including gastroesophageal reflux disease (GERD), non-ulcer dyspepsia (NUD), and diabetic gastroparesis, which affects half of all diabetes patients. The non-specific nature of delayed gastric emptying disorders often requires the rate of gastric emptying to be measured objectively. Measurement of gastric motility is achieved by monitoring the progression of a labeled test solid or liquid meal through the stomach. The rate of appearance of the label reveals information about the mechanics of gastric emptying.

The rate of gastric emptying can be influenced by many factors, including decreased fundic tone, decreased antral peristalsis, alterations in the gastric pacemaker, antropyloroduodenal incoordination, pyloric spasm, and intestinal dysmotility. Gastric emptying is also affected by a number of variables in test procedure, such as meal volume and temperature, the caloric density and nutritional content of the test meal, patient position and stress levels, patient gender and age, the technique of incorporating the label into the meal, and the method used for data acquisition and processing. In order to adequately study delayed gastric emptying, it is important that variations such as these should be minimized or otherwise accounted for.

The established diagnostic tool for monitoring solid and liquid phase gastric emptying is scintigraphic measurement of gamma emission from a radiolabeled test meal. The gamma emission from the radiolabel is visualized with a gamma camera held over the patient's abdomen and its progress from the stomach measured. This technique can be used to measure both solid and liquid phases of digestion, although the emptying of solids is generally of greater diagnostic significance.

Scintigraphy, however, is extremely costly and is limited by the availability of gamma cameras at clinical sites. More importantly, there are significant risks to the patient and the clinician associated with exposure to the radioactive tracer used in the scintigraphy. Further, the time required for the test is considerable, during which the patient must remain motionless under the gamma counter.

The expense and inconvenience of the scintigraphy test led to the creation of a simplified breath test. The breath test employs the metabolic reaction of 1-$^{13}$C-octanoic acid as a tracer of gastric activity, and is alternatively known as the "Octanoate Breath Test" or "OBT." Specifically, the $^{13}$C-octanoate breath test employs the stable isotope $^{13}$C, and gastric emptying is measured indirectly by monitoring the appearance of $^{13}CO_2$ in breath subsequent to ingestion and metabolism of the $^{13}$C-octanoate.

Octanoic acid is a naturally occurring eight-carbon fatty acid typically found in butter as an ester. It is a liquid at room temperature that is not water soluble. Generally, this and other medium chain fatty acids are efficiently absorbed by the small intestine and transported to the liver. In the liver, octanoic acid freely enters the mitochondria where it is oxidized to produce $CO_2$. Exhaled $CO_2$ is collected at regular intervals using a breath collection device and $^{13}CO_2$ content is measured with a mass spectrometer.

In the proposed invention, the Gastric Motility Breath Test (GMBT), the test meal is labeled with $^{13}$C-sodium octanoate, a water soluble solid. The test meal is administered after an overnight fast and breath samples are collected at 15 minute intervals over one to several hours. Mathematical analysis of the $^{13}CO_2$ appearance in breath reveals estimates of gastric emptying parameters. The first parameter is the lag time ($T_{lag}$). $T_{lag}$ corresponds to the trituration phase in which particles are selectively retained in the stomach until they become small enough to allow passage through the pylorus. $T_{lag}$ increases with delayed gastric emptying. The second parameter is the half emptying time ($T_{1/2}$). $T_{1/2}$ is the time at which half of the meal has passed through the stomach. $T_{1/2}$ increases when gastric emptying is delayed. The resulting curve reflects the sum influence of gastric emptying, digestion, absorption, and metabolism. The metabolic processing of octanoate is rapid and reproducible. Therefore, delays in emptying are due to differences in gastric motility.

The advantages of the breath test are that 1) there is no radioactivity exposure for the patient or clinician; 2) the test can be administered anywhere without need for specialized shielding equipment or disposal procedures; 3) there is no requirement for specialized training of personnel to handle the radioactivity; 4) increased convenience for the patient; and 5) it does not require access to expensive imaging equipment.

The original scintigraphy method required clinicians to mix radiolabeled tracer into scrambled eggs or chicken liver and cook the meal on site. Like the original scintigraphy method, the breath test is also administered with a scrambled egg or liver pate test meal. However, there are problems associated with using egg or liver for any type of gastric emptying test.

Specifically, there can be difficulty with uniform incorporation of the isotope into the egg or liver. To obtain radioactive liver, $^{99m}$Tc-SC is injected into the wing vein of a live chicken. The label is taken up by hepatic Kupffer cells resulting in an intracellular trapped label. Because this process is cumbersome, many centers switched to adding label to scrambled eggs.

For the egg-based tests, the yolk and egg white are first separated because the label is only readily solubilized in the yolk. The label is added to the yolk, which is then beaten. The egg white is added back and again beaten, followed by cooking. Alternatively, the labeled yolk is cooked entirely separately from the egg white, and the two components are mixed and digested together.

A second problem is that meal homogeneity is difficult to maintain. Eggs, for example, vary in caloric content, size and composition. In addition, improper and non-standardized cooking conditions can affect the outcome of the test and prevent the intra-clinic comparison of test results. Further, palatability was less than desirable, especially with the liver based test.

U.S. Pat. No. 4,985,232 teaches a standardized test meal combining radiolabel with freeze dried beef. The freeze dried beef was an attempt to offer a uniform delivery system that could be used in a standardized fashion in various clinics. Radiolabel was injected into the dried beef (in the form of beef stew) and the beef was then warmed and served to the patient. However, many patients prefer to avoid meat-based, especially red meat-based tests, either due to a vegetarian life-style or because of various health concerns associated with consuming such a product (most beef stews are high in sodium and fat). Furthermore, the body digests and metabolizes carbohydrates far more efficiently and completely than fat and protein. Thus, a meat based test will require more time to perform than a carbohydrate based test. Finally, this test meal was designed for use with scintigraphy, and is thus limited because it is used with radiolabel. Furthermore, it is likely that $^{13}C$-octanoate could not be stably incorporated into a dried beef-based meal.

Alternative methods of delivery of the $^{13}C$-octanoate have been developed, but still do not meet all the clinical needs of diagnostic physicians. Specifically, two related tests were developed that both use the breath test. U.S. Pat. No. 5,707,602 teaches a pre-cooked algae biscuit that incorporates the $^{13}CO_2$ directly into the biscuit by preparing the biscuit with an algae such as *Spirdina Platensis* that was grown in a 99% $^{13}CO_2$ environment. Pre-cooked products of course have a shorter shelf-life than dry mixes. In addition, the incorporation of label directly into the biscuit presents FDA regulatory hurdles that must be addressed, which can be avoided by not mixing the label into a food product. Additionally, the growing of algae under specialed conditions presents additional expense, increasing the cost of the final test. Further, the algae may cause an adverse allergic reaction in a patient and may be less than palatable. U.S. Pat. No. 5,785,949 teaches a similar $^{13}CO_2$-grown algae drink. This delivery system only allows the measurement of liquid emptying, which may not be affected in many gastric disorders. Further, it suffers from the same disadvantages that the algae biscuit has.

Thus, there is still a need in the art for a palatable, easy to use, meat-free, standardized test meal that can be administered in conjunction with a $^{13}C$-octanoate breath test.

SUMMARY OF THE INVENTION

The invention in one of its embodiments, is a standard meat-free test meal kit for measuring gastric motility of solids, where the kit contains at least a tracer and a meat-free, test meal dry mix that is about 50%–90% carbohydrate, 10%–30% fat, 0–30% protein, and is between about 150 and 500 kcal. The kit may also have a container suitable for mixing and cooking a test meal, a breath collection device, a cooking device, a stirring implement, a temperature indicator, a sample label, a mix reconstituting fluid, and evacuated tubes. A method of measuring delayed gastric emptying using the kit is also provided.

The test meal serves as a caloric challenge and retains the tracer while digestion occurs. In the preferred embodiment, the tracer is labeled with a stable isotope. The proposed test meal offers several advantages over the current state-of-the-art including ease of preparation and standardization of composition. and calorie content. In addition, an alternative to a meat containing formulation is preferable to individuals who choose a vegetarian diet. In the preferred mode, the meal components (dry mix, isotope, and liquid) are reconstituted and cooked on site prior to administering the test. On site preparation of the pre-packaged test meal reduces variability associated with storage of a pre-cooked meal. This formulation also provides commercial advantages since a dry mix has a long shelf life and does not require special handling. This embodiment constitutes a significant improvement over current methodologies and formulations because it allows accurate standardization of gastric emptying results for the first time.

DETAILED DESCRIPTION OF THE INVENTION

Figure 1:
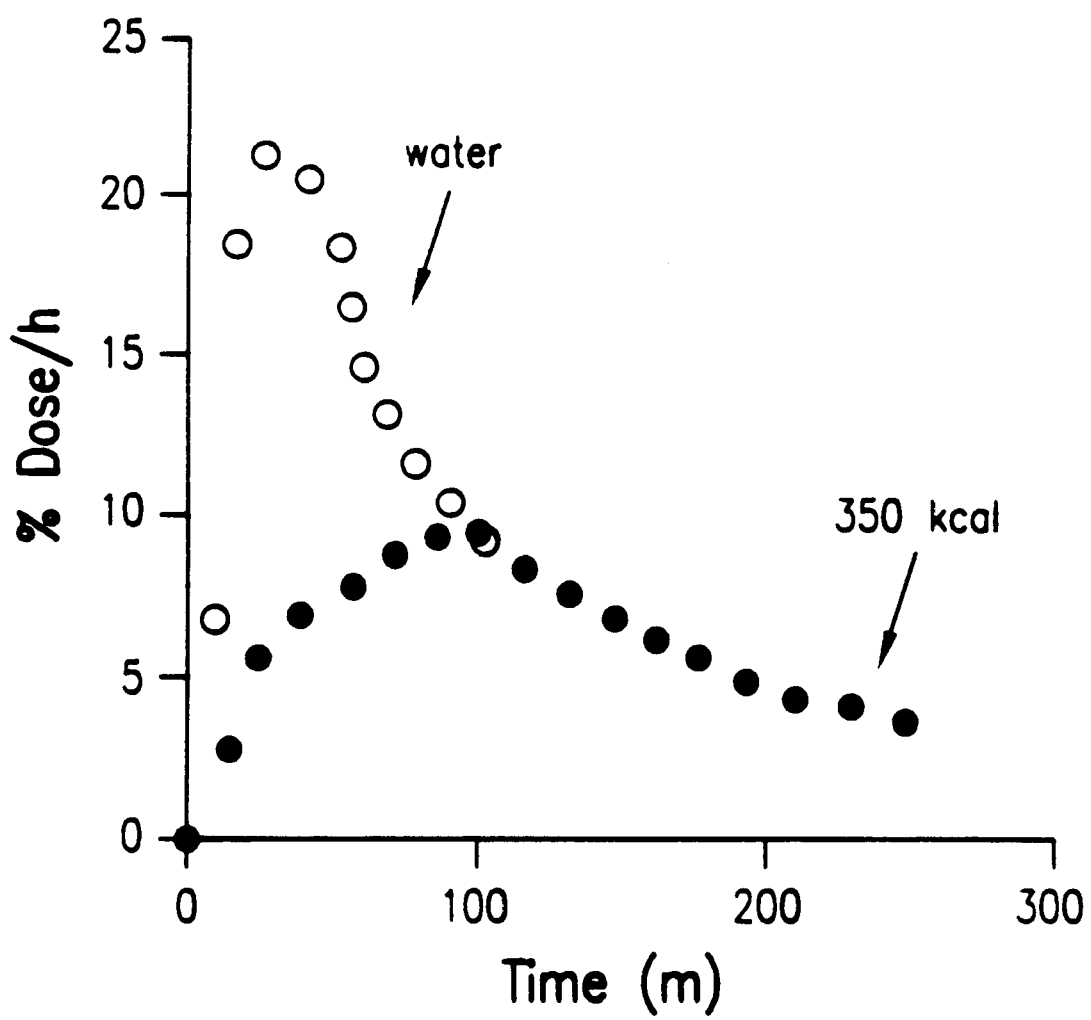
FIG. 1. Appearance of $^{13}CO_2$ in breath.

In this invention the following terms are used as follows: "A" device or "an" element. The word "a" or "an" used in the kit claims to introduce a kit component is intended to mean that one or more of the recited components may be present in the kit.

Breath collection device means complete breath collection devices, or a disposable parts thereof, such as bags, evacuated tubes, mouthpieces, etc.

Carbohydrate is defined herein to include all sugars, starches, and cellulose and derivatives, including monosaccharides, disaccharides, and polysaccharides.

Fat is defined herein to include a fatty acid or ester or derivative thereof, or di- and tri-acyl glycerides and derivatives thereof.

Gastric Motility Breath Test (GMBI) denotes the proposed invention described herein.

Protein is defined to include all amino acides, dipeptides, and polypeptides, including hydrolyzed proteins and/or derivatives of proteins.

Standard or standardized means that each kit sold and or test performed is substantially identical to each other kit or test, such that results may be compared from one clinic to another.

Test meal dry mix means a dry mix (such as is commonly found in supermarkets), which optionally may contain tracer, which is reconsitituted with liquid, and tracer if not already contained therein, to form a test meal. The test-meal dry mix described and claimed herein is both meat-free and algae-free, although it may contain yeast or yeast remnants.

Tracer is defined herein to be any substance that can be traced as it passes from the stomach. The tracer may comprise a fatty acid, or fatty acid esters, salts, glycerides or derivatives thereof, including but not limited to octanoate, decanoate, dodecanoate, and tetradecanoate, and preferably any stable isotope, including but not limited to $^2H$, $^{13}C$, $^{15}N$, and $^{18}O$. The fatty acid is preferably labeled in position 1 of the molecule, in the metabolically active position of the labeled molecule, or may contain any plurality of labeled atoms. Additionally, the tracer may be a dye, magnetic, metal, or a metabolically inert compound, provided only that the tracer travel through the stomach at a rate comparable to the nutritional solids and the tracer can be measured in the blood, urine, breath or followed in situ by some visualizing means.

This invention provides a standardized test meal and kits which are convenient to use, have unlimited shelf life, and which are in a form that is palatable to most patients. A variety of factors must be standardized in order to provide a test meal that provides gastric emptying results that can be compared from clinic to clinic.

Thoroughly incorporating the label into the meal is essential. Poor labeling of the solid phase of the meal may result in separation of the label from the solid phase into the liquid phase. Because liquids empty faster, this could lead to a normal gastric emptying value in a patient who suffers from delayed emptying. Stable incorporation may be determined by incubating the test meal at 37° C. in gastric juices, and measuring the amount of label leached into the gastric juices over time.

The test meal must offer clinicians a standardized recipe that has fixed carbohydrate/protein/fat proportions. The test meal has an ideal constituency of:

0–60% fat, preferably 5–25% fat, and most preferred about 20% fat (all percentages herein given as dry weight percentage); 50–90% carbohydrate, preferably 60–80%, and most preferred about 70% carbohydrate; 0–30% protein, preferably 5–25%, and most preferred about 10% protein; and between 100 to 500 kilocalories (Kcal), preferably between 150–400, and most preferred about 250 to 350 Kcal.

The raw ingredients include, but are not limited to, enriched bleached flour, enriched flour, sugar, yellow corn flour, whole wheat flour, leavening, partially hydrogenated soybean oil, vegetable shortening, oat bran, rolled oats, nonfat milk, buttermilk, molasses, malted barley, salt, egg white, food starch-modified, whey, dextrose, emulsifier, defatted soy flour, soy lecithin, natural and artificial flavors, and spices. These ingredients may be standardized in any amount that creates a muffin, cake, donut, cookie, pancake or any other easily cooked test meal that will stably incorporate the chosen tracer.

The test meal may be presented in a variety of formats, including but not limited to muffin, cake, donut, cookie, pancake, french toast, waffle, and tarts. Any format may be used, the only criteria for selection being convenience, stable incorporation of the tracer, palatability and being amendable to standardization for the measurement of gastric emptying.

Preparation of the test meal can be standardized by cooking in either a table top convection oven between 250°–400° F. for two to twenty minutes, or in a microwave oven for one to four minutes on a medium to high cooking power setting. Simple tests will determine the optimal cooking period and temperature, or microwave wattage for the test meal format chosen.

Figure 4:
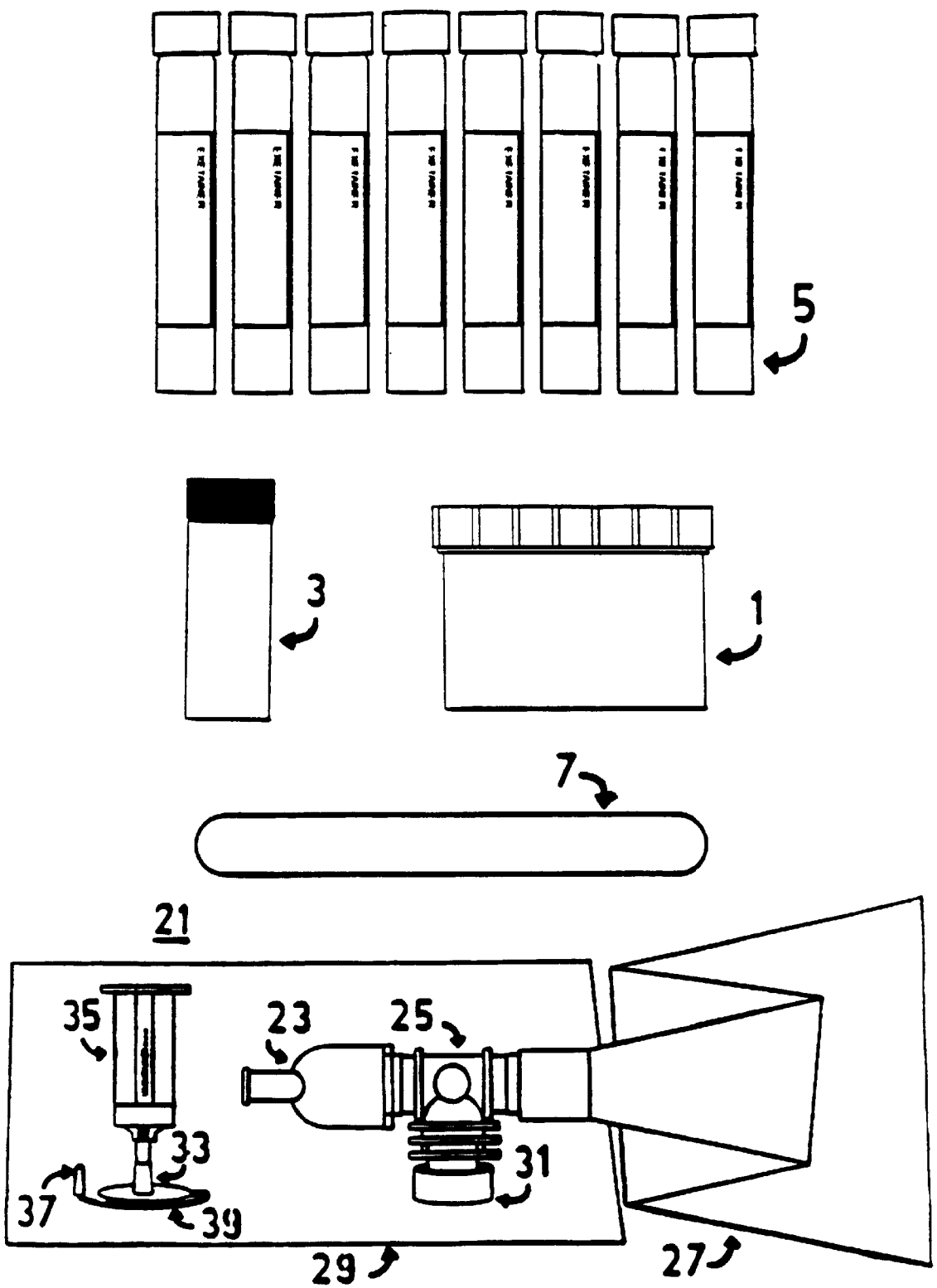
FIG. 4. Diagram of kit with each component illustrated.

In one embodiment of the invention, a complete kit for the providing of a delayed gastric emptying breath test is provided, as shown in FIG. 4. The kit contains a standardized test meal dry mix (not shown), which may be shipped in a foil or plastic covered container 1 that is also suitable for both mixing and cooking the meal. Alternatively, the test meal may be shipped in any other conventional packaging means, such as a foil pouch. The kit may also contain other elements such as a tracer 3, stirring implement 7 such as a spoon or bar, breath collection device 21 with evacuated tubes 5, such as Vacutainer™ or Exetainer™ tubes, or just evacuated tubes 5. In one embodiment, a convection oven or microwave is packaged with the first test kit provided to a given clinic, in order facilitate standardized cooking conditions. Replacement kits contain only the test meal, container, tracer and optionally a disposable breath collection device or evacuated tubes. Other elements that may be packaged into kits for the convenience of the user include a measured amount of mix reconstitution fluid, such as water or juice, a temperature indicator such as a plastic indicator strip that may be affixed to the container or provided separately, and sample labels for adequately identifying the samples collected.

Breath collection devices are extensively used for diagnostic purposes, including testing for alcohol, ketones, *Helicobacter pylori*, as well as gastric emptying. Thus, breath collection devices are well known in the art and include, as examples, the devices illustrated or described in U.S. Pat. Nos. 5,848,975, 467,776, 5,465,728, 5,432,094, 5,361,772, 5,327,901, 5,291,898, 5,211,181, 5,140,993, 5,081,871, 5,071,769, 5,026,027, 4,947,861, 3,867,099, and D0304232, all of which are hereby incorporated by reference.

The complete breath collection device preferred herein is a simple, inexpensive disposable device marketed by Quintron,™ as Quintron Multi-Patient Collection Bag, 750 ml (Part #QT00841-P); Tee Piece (Part #QT00850-P); Mouthpiece, Universal (Part #QT00991-P); Gasampler Discard Bag, 400 ml (Part #QT00843-P). This complete breath collection device 21 is composed of a mouthpiece 23, which is joined to a tee-piece 25, which is joined to a discard bag 27. The tee-piece is connected to a breath collection bag 29, via a one way valve 31. The breath collection bag also has a sample port 33 with a needle (not shown) that is connected to a evacuated tube adaptor 35 into which a evacuated tube can be inserted (as shown) for sample collection. The bag also contains a plug 37 with tether 39 which can be used to plug the sample port if desired.

In operation the device is assembled and the patient blows into the mouth piece and the initial breath flows freely into the discard bag. When the discard bag is full, the pressure forces open the one way valve, allowing breath from deeper in the lungs to fill the collection bag. One or more samples of this later breath can be collected by inserting a evacuated tube into the evacuated tube adaptor on the sample port. The kit may contain one or more complete breath collection devices, and one or more vacuum tubes, bags, mouthpieces, etc. for multiple sample collections.

The test meal can be served at a variety of temperatures, but since temperature influences the rate of gastric emptying, the temperature should be standardized. Accordingly, the serving temperature which will preferably be room temperature (approximately 25° C.), but may be cooler (between 4°–25° C.), or warmer (between 26°–45° C.).

The preferred tracer is $^{13}C$-otanoate, but can also include any molecule with a predictable digestive route, including but not limited to fats, carbohydrates, proteins, amino acids, or non nutrient molecules that pass through the stomach at a rate comparable to the rate in which solids are emptied. The preferred label is a stable isotope, such as $^{13}C$, but can also be $^2H$, $^{15}N$, and $^{18}O$ or any other stable isotope.

In a preferred embodiment, the patient will arrive at the clinician's facility after an overnight fast and have a baseline level of exhaled $CO_2$ measured. The test meal in one of its possible physical forms will be consumed while the patient is either calmly resting in a horizontal position or alternatively, in a comfortable seated or reclining position. Preferably, these conditions, as well as lighting and temperature, are standardized. The patient's exhaled $CO_2$ will then be collected in the breath collection device and the appearance and rise of $^{13}CO_2$ will be measured as a function of the rate of gastric emptying. The collection will continue from 1–6 hours, depending on the mode of measurement.

Specifically, one embodiment of the invention consists of a pre-measured quantity of dry mix ingredients provided as a complete test meal kit. The kit will contain the following:

(a) dry muffin or cake mix to make a standard, specific kcal meal;

(b) a tracer, such as $^{13}$C-octanoate, or salt or derivative thereof; optionally, (c) container for mixing dry ingredients with liquid in which the test meal can be cooked or otherwise prepared; optionally, (d) a breath collection device; and optionally, (e) a cooking device, such as a small portable microwave oven, a stirring implement, a temperature indicator, dry mix reconstitution fluid, extra evacuated tubes and sample labels.

The test is administered according to a fully standardized procedure, such as the following:

(1) Dry mix, water, and tracer are mixed thoroughly.

(2) The mix is cooked exactly as directed, and cooled to room temperature.

(3) The patient arrives at the clinic after an overnight fast.

(4) A baseline sample may be collected from the patient.

(5) The test meal is administered, preferably with a measured amount of water. The patient remains in a similar position throughout the test. Preferably, the patient remains sitting erect (as opposed to slumping) in a chair, or fully reclining in a reclining chair.

(6) Continue sample collection for the duration of test. The appearance of label is measured appropriately.

EXAMPLE 1

Test Meal

A dry mix composition is prepared as follows:

| | |
|---|---|
| Calories | 350.84 |
| Calories from fat | 70.48 |
| Total Fat | 7.56 g |
| Saturated Fat | 1.51 g |
| Polyunsaturated Fat | 3.07 g |
| Monounsaturated Fat | 1.02 g |
| Cholesterol | 9.78 mg |
| Sodium | 786.61 mg |
| Potassium | 0.00 |
| Total Carbo. | 63.01 g |
| Dietary Fiber | 3.02 g |
| Sugars | 22.19 g |
| Protein | 8.00 g |
| Vitamin A | 0.00% |
| vitamin D | 0.00 |
| Vitamin C | 0.00% |
| Calcium | 6.05% |
| Iron | 13.96% |

-continued

| | |
|---|---|
| thiamin | 14.67% |
| riboflavin | 9.78% |
| niacin | 7.83% |
| Folic acid | 9.78% |

Fat percentage may be increased to prolong the period of gastric emptying or decreased to provide a low calorie meal, as preferred. The ingredients included enriched bleached flour (wheat flour, niacin, reduced iron, thiamin mononitrate, riboflavin), enriched flour (wheat flour, malted barley flour, niacin, iron, thiamin mononitrate, riboflavin, folic acid), sugar, yellow corn flour, whole wheat flour, leavening (baking soda, sodium aluminum phosphate, monocalcium phosphate, aluminum sulfate), partially hydrogenated soybean oil, vegetable shortening partially hydrogenated soybean/or cottonseed oil), oat bran, rolled oats, nonfat milk, buttermilk, molasses, malted barley, salt, egg white, food starch-modified, whey, dextrose, emulsifier (propylene glycol monoester, monoglycerides, sodium stearoyl lactylate), defatted soy flour, soy lecithin, natural and artificial or natural flavors, and spices. The ingredients were mixed to produce a dry mix which could be used to prepare the test meal.

In preparing the test meal, 64–90 g of dry mix ingredients were mixed with 42–60 g of water and 100 mg of $^{13}$C-octanoate in a microwave safe, muffin-appropriate container. After mixing thoroughly, the mix was placed into a 700 watt microwave and cooked on high for 1 minute to 3 minutes. The muffin was cooled to room temperature before use.

EXAMPLE 2

Impact of $^{13}$C-sodium Octanoate

An experiment was conducted to show that $^{13}$C octanoate label can be successfully incorporated into the standard test meal. Specifically, this experiment was designed to determine to what extent octanoate absorption and metabolism influenced the characteristics of the gastric emptying curves. Results from one participant are given here and are typical of results obtained from other participants in the study (Mean +/−1 SD, $T_{1/2}$=68.6+/−9.2, $T_{lag}$=33.8+/−7.2, n=3). In this example, a healthy adult male was administered $^{13}$C-sodium octanoate following two different protocols. The first test consisted of a 100 mg bolus of $^{13}$C-sodium octanoate administered with 150 ml water. Breath was collected at 10 minute intervals for a period of 2 hours. For the second test, 100 mg $^{13}$C-sodium octanoate was administered following a standard protocol with a 350 Kcal standard muffin test meal and 150 ml water. Breath was collected every 15 minutes for a period of 4 hours. Results from the $^{13}CO_2$ appearance curves are plotted in FIG. 1.

Mathematical analysis of the later-derived curve gave a $T_{lag}$ and $T_{1/2}$ of 39 and 61.5 minutes, respectively. Although the octanoate label does require processing prior to its appearance in breath, appearance is rapid and highly reproducible. As such, it does not adversely impact the duration of the breath test or, as is discussed in subsequent sections, the ability to distinguish varying degrees of gastric emptying.

These results show that $^{13}$C-octanoate is successfully incorporated into the muffin test meal and that the metabolism of the labeled muffin allows measurement of the rate of gastric emptying in a fashion that is not adversely affected by the muffin itself.

EXAMPLE 3

Reproducibility

Reproducibility of the 350 kcal standard muffin test meal was investigated in seven volunteers on two occasions (Test 1 and 2) within a one-week period using the GMBT. Test meals were administered on the morning after an overnight fast and breath was collected at 15 minute intervals for 3–4 hours. The results for the gastric emptying data are given in table 1.

TABLE 1

$T_{lag}$ and $T_{1/2}$ reproducibility data from two independent test meal administrations using the GMBT.

| Participant | Test 1 | | Test 2 | |
| --- | --- | --- | --- | --- |
| | $T_{lag}$ | $T_{1/2}$ | $T_{lag}$ | $T_{1/2}$ |
| 001 | 67.3 | 103.6 | 77.1 | 127.3 |
| 002 | 76.1 | 136.0 | 74.2 | 108.5 |
| 003 | 94.4 | 181.3 | 99.6 | 190.7 |
| 004 | 84.2 | 123.8 | 69.5 | 109.8 |
| 006 | 104.5 | 167.0 | 90.3 | 176.3 |
| 007 | 82.2 | 125.3 | 70.7 | 118.0 |
| 008 | 103.9 | 146.7 | 88.6 | 127.8 |
| Mean* | 87.5 | 140.5 | 81.4 | 136.9 |
| SD | 14.0 | 26.7 | 11.5 | 33.0 |
| % RSD | 16.0 | 19.0 | 14.1 | 24.1 |

*Difference in $T_{lag}$ or $T_{1/2}$ was not statistically significant. A paired student's t-test yielded p = 0.173 for T lag and p = 0.621 for $T_{1/2}$. Participant 005 did not complete both independent test meal administrations.

The reproducibility of gastric emptying parameters determined with the GMBT did not differ significantly between the two test periods. Inter-subject variability is comparable to that reported in the literature for breath-based gastric emptying tests.

EXAMPLE 4

Sensitivity of the GMBT

Figure 2:
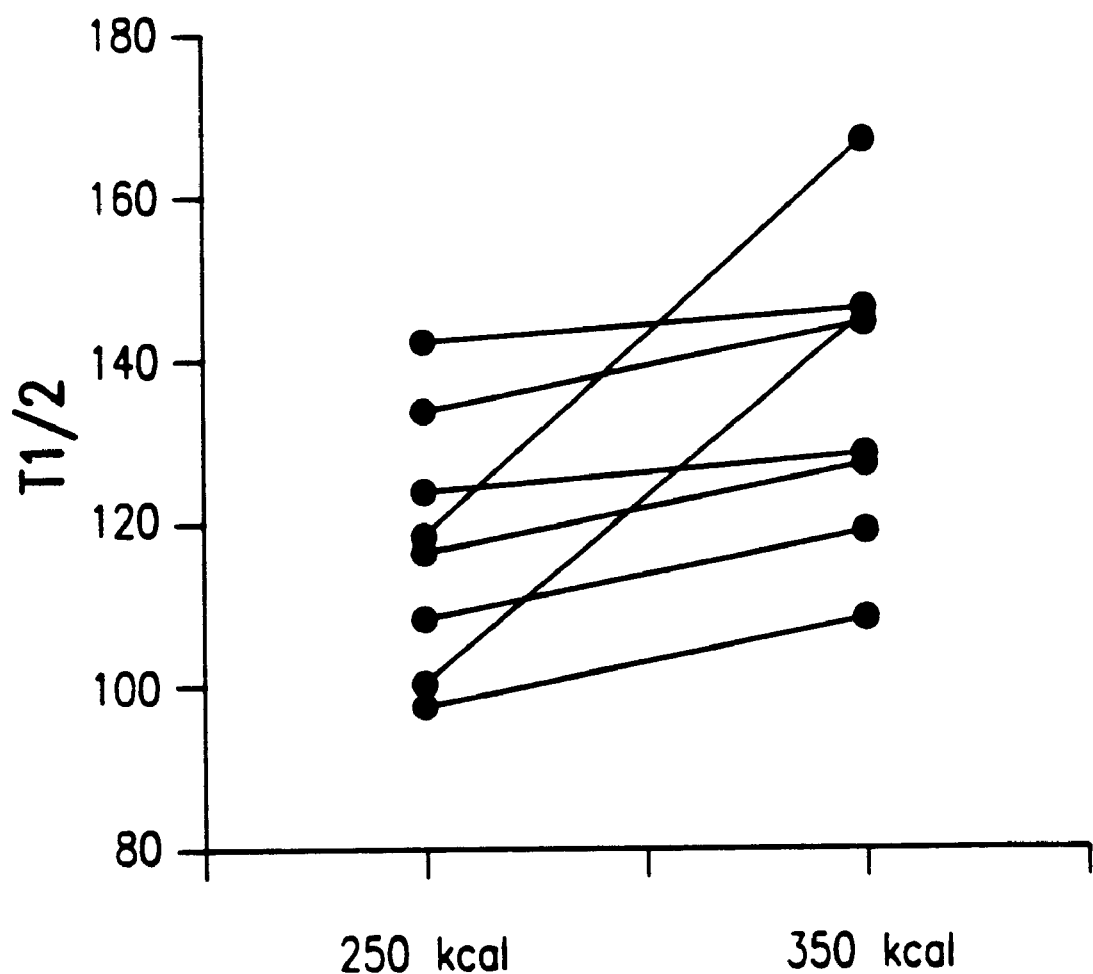
FIG. 2. Plot of $T_{1/2}$ derived from using two proposed test meals with different caloric content.

An experiment was conducted to determine the ability of the GMBT to detect small changes in gastric motility induced by different test meal sizes. This protocol simulates differences in gastric emptying parameters that might be observed during a typical investigation. In this experiment, one each of a 250 and 350 kcal muffin test meal was administered in randomized fashion to eight volunteers within a one-week period. Test meals varied only in their caloric content and size, not in their composition. Analysis of the data revealed a significant difference for $T_{1/2}$ and $T_{lag}$ using a paired t-test at 95% confidence ($T_{1/2}$, p=0.004 and $T_{lag}$, p=0.02). a plot of the $T_{1/2}$ data is given in FIG. 2.

This data shows that the labeled test meal is sensitive enough to give results that reflect small changes in the volume of the test meal. It can be concluded that the test meal is ideal for accurately measuring the normal ranges of gastric emptying rates associated with different average meal sizes. Specifically, this data supports the ability of the GMBT to detect a 20% difference

EXAMPLE 5

Influence of a Promotility Agent

Figure 3:
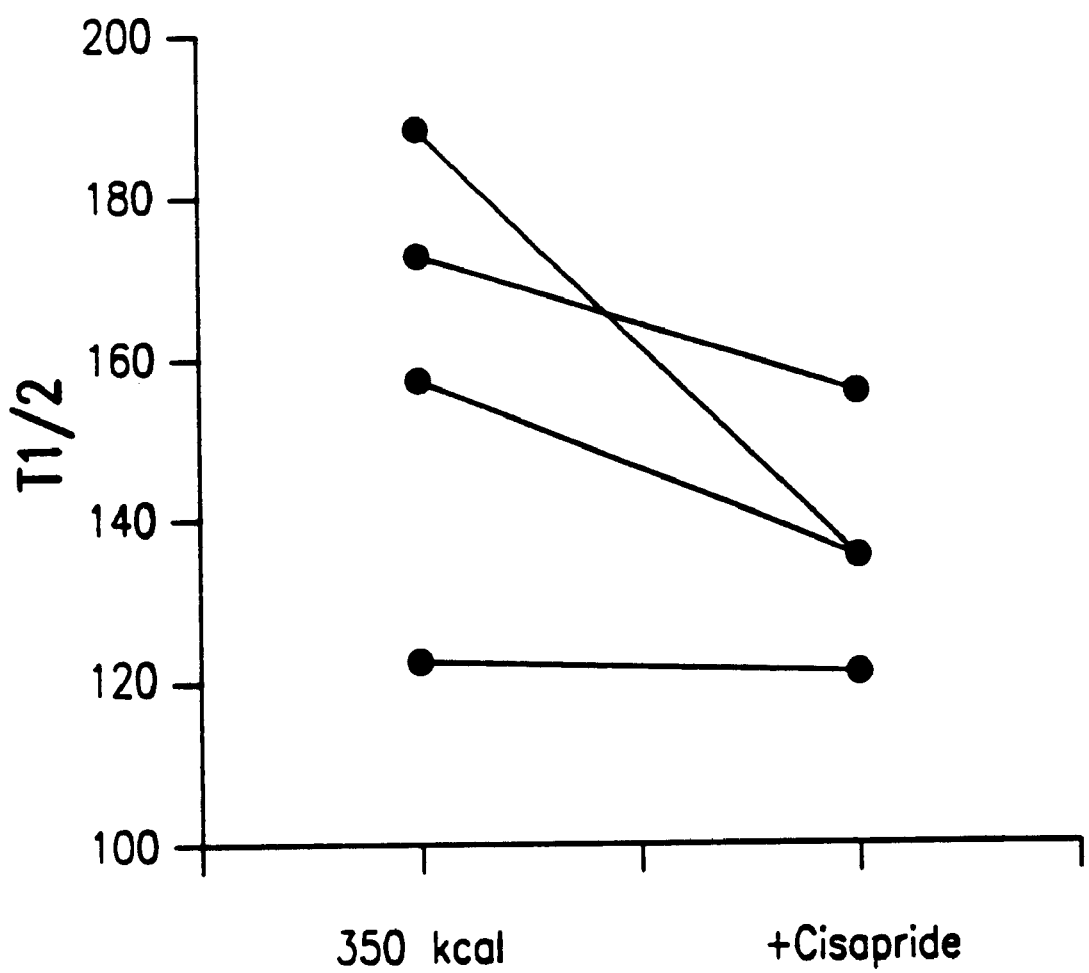
FIG. 3. Influence of a promotility agent on $T_{1/2}$ measured with the GMBT.

An experiment was done to examine the ability of the GMBT to detect changes introduced by the promotility agent, Cisapride. Gastric emptying tests employing a 350 kcal muffin test meal were administered on two occasions within a one-week period. One test was conducted as a control. The other test was conducted after treatment with Cisapride. Cisapride (10 mg) was administered at 10:00 P.M. on the evening prior to the test and one half hour before administration of the muffin test meal. Gastric emptying results for the control meal were delayed relative to the meal administered with Cisapride. In spite of a small data set, $T_{1/2}$ proved to be statistically different for the two meals at p=0.05. $T_{lag}$ did not show significance, p=0.21. FIG. 3 shows a plot of the results for the $T_{1/2}$ data with and without treatment with Cisapride.

Investigation of the effects of a promotility agent revealed a significant decrease in $T_{1/2}$ using the GMBT. A similar trend was evident, but not significant for the $T_{lag}$. In spite of a small data set, the test was able to detect changes in $T_{1/2}$ in a small experimental group induced by the promotility agent Cisapride.

EXAMPLE 6

Comparison with the Prior Art

The standard muffin test meal was compared against the scrambled egg prior art test meal. Unfortunately, a freeze dried beef test meal was not available for comparison. The results (not shown) indicate that a comparably sized egg meal empties slower than the muffin meal (about a 30–40% delay). Most likely this discrepancy is a result of the higher fat content of the egg meal. This is consistent with reports in the literature that indicate fats delay gastric emptying. Judging from the preliminary studies, the muffin test meal offers a faster test without sacrificing its diagnostic ability.

PROPHETIC EXAMPLE 7

Optimal Cooking Temperature

An experiment will be done to ascertain the optimal temperature and conditions for cooking the standard muffin test meal. The results of this experiment provide information about the optimal way to prepare the test meal. The test meal will be prepared in a convection oven at several test temperatures and for several cooking periods. Specifically, the test meal will be cooked at 250° F., 300° F. 350° F. and 400° F. for 10, 12, and 15 minutes at each temperature. Similarly, the test meal will be cooked in microwaves of varying wattage (power setting maximum) for 1, 1.5, 2, and 3 minutes. Depending on the test meal format, other cooking devices, such as toaster ovens, toasters, waffle irons, etc. may also be evaluated. The test meals will be evaluated for convenience, consistency, palatability and stable incorporation of tracer. An appropriate and convenient cooking protocol will be chosen from this experiment.

PROPHETIC EXAMPLE 8

Optimal Serving Temperature

An experiment will be done to ascertain the optimal temperature at which to serve the muffin test meal. This experiment will be carried out by administering the test meal to a test population at room temperature (approximately 20–25° C.), 4° C. and 35° C. on different days. The test meal composition and volume will not be changed. It is expected that increased temperature will decrease the rate of gastric emptying and a standard, convenient and palatable serving temperature will be recommended.

PROPHETIC EXAMPLE 9

Collection of Normal Values

An experiment is performed to collect gastric emptying data from a large number of normal volunteers in order to provide normal clinical parameters for varying age groups and sex of individual. Gastric emptying in women is generally slower, particularly in the final two weeks of the menstrual phase. Increased age may decrease gastric emptying rates. The same test meal will be administered under standard conditions to different groups divided by gender and age. Normal gastric emptying parameters will be determined for each test group.

What is claimed is:

1. A method of measuring delayed gastric emptying, said method consisting of:
   (a) reconstituting a solid test meal consisting of a dry mix and a $^{13}C$ tracer and a fluid by mixing the dry mix and the $^{13}C$ tracer and the fluid;
   said dry mix consisting of 50%–90% carbohydrate, 5%–60% fat, 5%–30% protein, between 100 and 500 kcal, and being meat-free and algae-free,
   said $^{13}C$ tracer selected from a group consisting of fatty acids, fatty acid esters and glycerides,
   said fluid being water or juice;
   (b) cooking the test meal;
   (c) cooling the test meal;
   (d) administering the test meal to a patient;
   (e) collecting breath samples from the patient; and
   (f) measuring the amount of $^{13}CO_2$ therein and determining therefrom the gastric emptying of the patient.

2. The method of claim 1, wherein the test meal consists of 60%–80% carbohydrate.

3. The method of claim 2, wherein the test meal consists of 5%–25% protein.

4. The method of claim 3, wherein the test meal consists of 5%–25% fat.

5. The method of claim 4, wherein the calorie content of the test meal is between 150–400 kcal.

6. The method of claim 1, wherein said $^{13}C$ tracer is a fatty acid or salt thereof between 8 and 14 carbons.

7. The method of claim 1, wherein said $^{13}C$ tracer is $^{13}C$-1-octanoate or a salt thereof.

8. The method of claim 6, wherein the test meal is 5–25% fat, 50–90% carbohydrate; 5–25% protein; and between 150 to 400 Kcal.

9. The method of claim 7, wherein the test meal is about 20% fat, about 70% carbohydrate; about 10% protein; and between 250 to 350 Kcal.

10. The method of claim 1, 8 or 9, wherein said test meal dry mix is reconstituted to produce a test meal of a format selected from the group consisting of muffin, cake, donut, cookie, pancake, french toast, waffle or tart.

11. The method of claim 1, 8 or 9, wherein said test meal dry mix is reconstituted to produce a test meal of a format of a muffin.

12. The method of claim 1, 8 or 9, wherein the $^{13}C$ tracer is combined with the test meal dry mix.

13. The method of claim 1, 8 or 9, wherein the $^{13}C$ tracer is provided separately from the test meal dry mix.

14. A method of measuring delayed gastric emptying, said method consisting of:
   (a) reconstituting a solid test meal consisting of a dry mix, a $^{13}C$ octanoate tracer and water or juice, by mixing the dry mix and the $^{13}C$ octanoate tracer and water or juice;
   said dry mix consisting of 60–80% carbohydrate, 5–25% fat, 5–25% protein, being between 250–350 kcal, and being meat-free and algae-free;
   (b) cooking the test meal to form a muffin;
   (c) cooling the test meal;
   (d) administering the test meal to a patient;
   (e) collecting breath samples from the patient; and
   (f) measuring the amount of $^{13}CO_2$ therein and determining therefrom the gastric emptying of the patient.

15. A kit for carrying out the method of claim 1, consisting of:
   (a) a pre-measured quantity of meat-free, algae-free dry mix to make a standard meal between 100 and 500 kcal that is 50%–90% carbohydrate, 5%–60% fat, and 5%–30% protein;
   (b) a tracer that is $^{13}C$-1-octanoate or its salt; and,
   (c) a container for mixing and cooking the dry mix and the tracer with a fluid that is water or a juice.

16. A kit for carrying out the method of claim 1, consisting of:
   (a) a pre-measured quantity of meat-free, algae-free dry mix to make a standard meal between 100 and 500 kcal that is 50%–90% carbohydrate, 5%–60% fat, and 5%–30% protein;
   (b) a tracer that is $^{13}C$-1-octanoate or its salt;
   (c) a container for mixing and cooking the dry mix and the tracer with a fluid that is water or a juice; and,
   (d) a breath collection device.

17. A kit for carrying out the method of claim 1, consisting of:
   (a) a pre-measured quantity of meat-free, algae-free dry mix to make a standard meal between 100 and 500 kcal that is 50%–90% carbohydrate, 5%–60% fat, and 5%–30% protein;
   (b) a tracer that is $^{13}C$-1-octanoate or its salt;
   (c) a container for mixing and cooking the dry mix and the tracer with a fluid that is water or a juice;
   (d) a breath collection device; and,
   (e) one or more items selected from the group consisting of a cooking device, a stirring implement, a temperature indicator, a fluid that is water or juice, an evacuated tube and a sample label.

* * * * *